| United States Patent [19] | [11] Patent Number: 4,803,300 |
|---|---|
| Hijiya et al. | [45] Date of Patent: Feb. 7, 1989 |

[54] PROCESS FOR SEPARATION OF N-PROTECTED-α-L-ASPARTYL-L-PHENYLALANINES

[75] Inventors: Toyoto Hijiya, Kawasaki; Tadashi Takemoto, Yokkaichi; Toshihide Yukawa, Kawasaki, all of Japan

[73] Assignee: Ajinomoto Co., Inc., Tokyo, Japan

[21] Appl. No.: 84,162

[22] Filed: Aug. 11, 1987

[30]      Foreign Application Priority Data

Aug. 11, 1986 [JP]   Japan .................................. 61-188341

[51] Int. Cl.$^4$ .............................................. C07C 99/12
[52] U.S. Cl. ...................... 562/450; 530/801
[58] Field of Search .................... 530/801; 560/41; 562/401, 402, 450

[56]      References Cited

U.S. PATENT DOCUMENTS

| 3,786,039 | 1/1974 | Ariyoshi et al. | 560/41 |
| 3,933,781 | 1/1976 | Bachman et al. | 560/41 |
| 4,173,562 | 11/1979 | Bachman et al. | 560/41 |
| 4,480,112 | 10/1984 | Dryden et al. | 562/571 |
| 4,677,220 | 6/1987 | Tou et al. | 530/801 |
| 4,680,403 | 7/1987 | Hisamitsu et al. | 560/38 |

FOREIGN PATENT DOCUMENTS 0186378  7/1986  European Pat. Off. .............. 560/41

*Primary Examiner*—James H. Reamer
*Attorney, Agent, or Firm*—Oblon, Fisher, Spivak, McClelland & Maier

[57]      ABSTRACT

Disclosed herein is a process for separating N-protected-α-L-aspartyl-L-phenylalanine, more particularly a process for selectively separating N-protected-α-L-aspartyl-L-phenylalanine from a solution of N-protected-α-L-aspartyl-L-phenylalanine containing at least N-protected-α-L-aspartyl-D-phenylalanine as impurity.

6 Claims, No Drawings

PROCESS FOR SEPARATION OF N-PROTECTED-α-L-ASPARTYL-L-PHENYLALANINES

BACKGROUND OF THE INVENTION

The present invention relates to a process for separation of N-protected-α-L-aspartyl-L-phenylalanine.

α-L-aspartyl-L-phenylalanine methyl ester (aspartame) is known as an excellent sweetening agent, and various processes for preparing it have been proposed. However, since α-L-aspartyl-D-phenylalanine methyl ester which is a diastereomer thereof has no sweetness, no attempt has ever been reported on the use of D,L-phenylalanine as phenylalanine component in the preparation of aspartame and related compounds thereof. In the known processes, for example, in the processes for producing N-formyl-α-L-aspartyl-L-phenylalanine by condensing N-formyl-L-aspartic anhydride and phenylalanine in acetic acid (U.S. Pat. No. 3,933,781) or in an alkaline water medium (EP-A-No. 0186378), L-phenylalanine is used as phenylalanine component.

If it is made possible to use D,L-phenylalanine which is less expensive than L-phenylalanine for the preparation of aspartame, the preparation process will become more advantageous in industrial application since it is unnecessitated to obtain L-phenylalanine by optical resolution of D,L-phenylalanine or by asymmetric synthesis with a complicated procedure. However, when D,L-phenylalanine is condensed with, for example, an N-protected-L-aspartic anhydride, there are produced, in addition to the objective N-protected-α-L-aspartyl-L-phenylalanine (1), three other isomers, viz. N-protected-α-L-aspartyl-D-phenylalanine (2), N-protected-β-L-aspartyl-L-phenylalanine (3) and N-protected-β-L-aspartyl-D-phenylalanine (4) as shown below by chemical formulae:

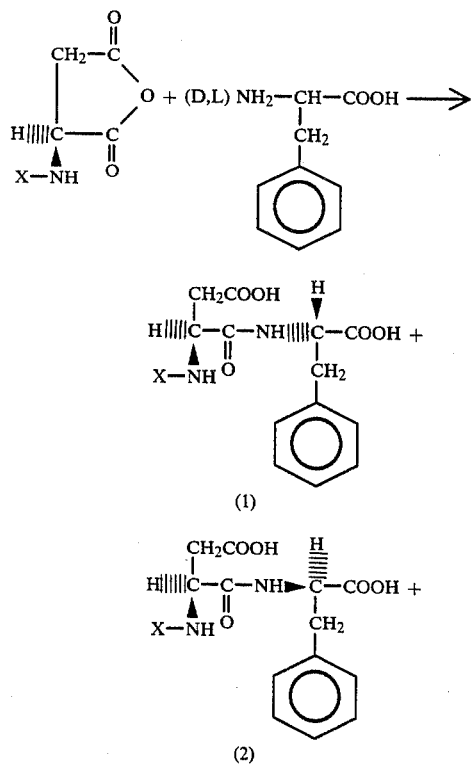
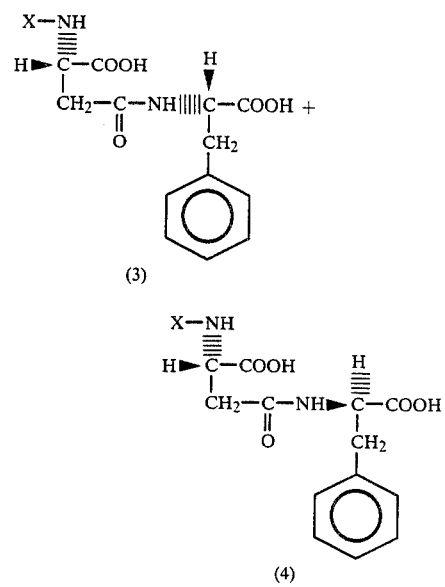

If it is possible to separate the objective N-protected-α-L-aspartyl-L-phenylalanine alone from a mixture of the four isomers, the separated compound (1) can be converted into α-L-aspartyl-L-phenylalanine methyl ester by a method comprising deformylation in a methanol/hydrochloric acid solution and successive esterification (U.S. Pat. No. 3,933,781) in the case where the protecting group is a formyl group, and thus an industrially advantageous aspartame preparation process can be provided.

However, as mentioned before, no report has ever been presented on the use of D,L-phenylalanine for the preparation of aspartame and related compounds thereof nor are available any data about the properties, especially solubility, of N-protected-α-L-aspartyl-D-phenylalanine and N-protected-β-L-aspartyl-D-phenylalanine produced by condensing N-protected-L-aspartic anhydride and D-phenylalanine, and accordingly there has yet been established no industrial process for selectively separating the desired N-protected-α-L-aspartyl-L-phenylalanine from a mixture of the four isomers.

In the prior art, the removal of the β-isomer (N-protected-β-L-aspartyl-L-phenylalanine) formed as a by-product when reacting N-protected-L-aspartic anhydride and L-phenylalanine, for example, in the case where the protecting group was a formyl group, has been carried out by separately precipitating the objective N-formyl-α-L-aspartyl-L-phenylalanine from an acetic acid solution (U.S. Pat. No. 3,933,781) or from an aqueous solution (EP-A-No. 0186378), leaving N-formyl-β-L-aspartyl-L-phenylalanine in the mother liquor. This removal of the β-isomer owes to the greater amount of formation and lower solubility of α-isomer than β-isomer. Regarding the amount of formation, that of N-formyl-β-L-aspartyl-L-phenylalanine is only about ⅓ to ¼ of that of N-formyl-α-L-aspartyl-L-phenylalanine in these methods.

On the other hand, in the case of using D,L-phenylalanine, the amount of N-protected-α-L-aspartyl-D-phenylalanine produced is almost equal to that of N-protected-α-L-aspartyl-L-phenylalanine, so that the removal of this isomer becomes the greatest problem.

As a result of studies for solving such problem, the present inventors found that N-protected-α-L-aspartyl-L-phenylalanine is less soluble in acetic solvents or aqueous solvents than N-protected-α-L-aspartyl-D-phenylalanine, so that the former alone can be precipitated out by a crystallization. It was further found that when N-protected-L-aspartic anhydride and D,L-phenylalanine are condensed in an acetic solvent or an aqueous solvent, the amount of N-protected-β-L-aspartyl-D-phenylalanine produced is as small as that of N-protected-β-L-aspartyl-L-phenylalanine and these two by-products are not precipitated in a crystallization operation, so that it is possible to separately crystallize N-protected-α-L-aspartyl-L-phenylalanine alone from a mixture of the four isomers. The present invention was attained on the basis of these findings.

SUMMARY OF THE INVENTION

In an aspect of the present invention, there is provided a process for separating N-protected-α-L-aspartyl-L-phenylalanine, which comprises selectively crystallizing N-protected-α-L-aspartyl-L-phenylalanine from an acetic solution or an aqueous solution of N-protected-α-L-aspartyl-L-phenylalanine containing at least N-protected-α-L-aspartyl-D-phenylalanine as impurity.

DETAILED DESCRIPTION OF THE INVENTION

The present invention relates to a process for selectively separating N-protected-α-L-aspartyl-L-phenylalanine from an acetic solution or aqueous solution of N-protected-α-L-aspartyl-L-phenylalanine containing at least N-protected-α-L-aspartyl-D-phenylalanine as impurity.

The aqueous solvent (solvent used in aqueous solution) or the acetic solvent (solvent used in acetic solution) used in this invention is not specifically restricted and any of the types of solvent can be used provided that it does not react with the four isomers. As the acetic solvent, there can be used acetic acid or mixtures of acetic acid and other organic solvents or water. As the aqueous solvent, water or mixtures of water and organic solvents miscible with water can be used. Such organic solvents can be selected, for example, from ethers such as diethyl ether, dioxane and tetrahydrofuran, hydrocarbons such as hexane and toluene, alkyl halides such as chloroform and ethylene dichloride, acetic acid esters such as ethyl acetate, alcohols such as methanol, ethanol and isopropanol, ketones such as acetone, carboxylic acids such as acetic acid and propionic acid, amides such as dimethylformamide, and acid anhydrides such as acetic anhydride.

The water to organic solvent mixing ratio, or the acetic acid to water or organic solvent mixing ratio is not critical in this invention; any mixing ratio can be employed if the mixed solvents are dissolved with each other to form a uniform mixture and also the three isomers other than the objective N-protected-α-L-aspartyl-L-phenylalanine are dissolved.

As the protecting group for amino group of aspartic acid component, it is possible to use those ordinarily employed for the peptide syntheses, such as formyl, acetyl, benzyloxy-carbonyl, t-butoxycarbonyl and the like.

When an acetic solution or an aqueous solution containing N-protected-α-L-aspartyl-L-phenylalanine (objective substance) and N-protected-α-L-aspartyl-D-phenylalanine is cooled after concentrating the solution if necessary, the objective substance separates out since the solubility thereof is lower than that of N-protected-α-L-aspartyl-D-phenylalanine.

Table 1 below shows the solubility of the two isomers in which the protecting group is formyl, that is, N-formyl-α-L-aspartyl-L-phenylalanine and N-formyl-α-L-aspartyl-D-phenyl-alanine.

TABLE 1

| Material | Solubility* | | |
|---|---|---|---|
| | at 20° C. | at 30° C. | at 40° C. |
| N—formyl-α-L-aspartyl-L-phenylalanine | 1.4 | 1.5 | 1.8 |
| N—formyl-α-L-aspartyl-D-phenylalanine | 4.0 | 5.1 | 7.4 |

*The solubility measured when acetic acid was used as solvent. Unit: g/dl.

The cooling temperature is preferably −5° to 50° C. The crystallization operation is ended before the other isomer separates out, and the separated objective substance is collected by filtration from the mother liquor, then washed and dried according to the conventional methods, whereby obtaining N-protected-α-L-aspartyl-L-phenylalanine having a purity of at least 90%.

When separating the objective substance from the aqueous solution of isomer mixture, it is preferable to adjust the pH of the solution to 1.0 to 3.5 with an inorganic acid such as hydrochloric acid, sulfuric acid, etc., or an organic acid such as citric acid or formic acid.

The above separation process can be applied to selectively separating the objective substance from a solution containing N-protected-α-L-aspartyl-L-phenylalanine (objective substance), N-protected-α-L-aspartyl-D-phenylalanine, N-protected-β-L-aspartyl-L-phenylalanine and N-protected-β-L-aspartyl-D-phenylalanine obtained by reacting N-protected-L-aspartic anhydride and D,L-phenylalanine in an acetic solvent or an aqueous solvent.

The reaction of N-protected-L-aspartic anhydride and D,L-phenylalanine is preferably carried out in the molar ratio of N-protected-L-aspartic anhydride to D,L-phenylalanine of 0.4–3.0. As for the mode of mixing N-protected-L-aspartic anhydride and D,L-phenylalanine, in the case of the reaction in an acetic solvent, there can be used either the method in which N-protected-L-aspartic anhydride is added to the solution of D,L-phenylalanine or the method in which D,L-phenylalanine is added to the solution of N-protected-L-aspartic anhydride, but generally the latter method provides a higher yield. In the case of the reaction in an aqueous solvent, the former method is preferred.

The condensation reaction, when carried out in an acetic solvent, proceeds smoothly at room temperature, but it is preferable to carry out the reaction at a temperature of 0° to 60° C. In the case where the condensation reaction is carried out in an aqueous solvent, the reaction is preferably carried out at a temperature not higher than 30° C. by keeping the pH of the solution at 7 or above, preferably 7 to 12.

Needless to say, D,L-phenylalanine used in the above reaction may not necessarily be a racemic modification.

For selectively separating the objective substance from an acetic solution or aqueous solution containing the four isomers, viz. N-protected-α-L-aspartyl-L-phenylalanine (objective substance), N-protected-α-L-aspartyl-D-phenylalanine, N-protected-β-L-aspartyl-L-phenylalanine and N-protected-β-L-aspartyl-D- phenylalanine obtained by said condensation reaction of N-protected-L-aspartic anhydride and D,L-phenylalanine, the same operations as in the case of selectively separating the objective substance from an acetic solution or aqueous solution containing the two isomers, viz. N-protected-α-L-aspartyl-L-phenylalanine (objective substance) and N-protected-α-L-aspartyl-D-phenylalanine described above may be employed.

When the acetic solution or aqueous solution of the four isomers is cooled preferably to −5° to 50° C. after concentrating the solution if necessary, the objective substance separates out first because the objective substance has the lowest solubility of the four isomers. In the case of carrying out the condensation reaction in an aqueous solvent, it is preferable to adjust the solution to pH 1.0 to 3.5 with an inorganic acid such as hydrochloric acid, sulfuric acid, etc., or an organic acid such as citric acid, formic acid, etc., prior to the crystallization.

The precipitated objective substance is separated from the mother liquor by suitable means such as filtration before other isomers separate out, and the separated substance is washed and dried. In this way, there can be obtained N-protected-α-L-aspartyl-L-phenylalanine having a purity of at least 90%.

As described above, according to the separation process according to the present invention, the separation of N-protected-α-L-aspartyl-L-phenylalanine and N-protected-α-L-aspartyl-D-phenylalanine, which has been unknown in the past, can be accomplished very easily. Further, the separation process of this invention makes it possible to use D,L-phenylalanine, which is less expensive than L-phenylalanine, for the formation of intermediate in the production of aspartame, in which L-phenylalanine has been used in the prior art.

The present invention will be described in more detail referring to the following non-limitative examples.

In the examples shown below, high performance liquid chromatography (hereinafter referred to as HPLC) was carried out under the following conditions:
Column: YMC Pack A-312 (ODS) 6 mm $\phi \times$ 150 mm
Mobile phase: 15% methanol, 0.2M $NaH_2PO_4$ (pH 4.5)
Flow rate: 1.0 ml/min
Temperature: 40° C.
Detection: 210 nm

EXAMPLE 1

N-formyl-α-L-aspartyl-L-phenylalanine (0.30 g (0.97 mmol)) and N-formyl-α-L-aspartyl-D-phenylalanine (0.30 g (0.97 mmol)) were dissolved in 12 ml of 1N NaOH. The pH of the solution was adjusted to 3.0 by adding 6N HCl. One hour later, the pH was reduced to 1.4 and the solution was allowed to stand at room temperature overnight.

The precipitated crystals were separated by suction filtration, washed with a small quantity of cold water and dried in vacuo to obtain 0.20 g of crystals. The result of HPLC analysis of the product showed that it was N-formyl-α-L-aspartyl-L-phenyl-alanine of 98.7% purity.

EXAMPLE 2

N-formyl-α-L-aspartyl-L-phenylalanine (0.50 g (1.62 mmol)) and N-formyl-α-L-aspartyl-D-phenylalanine (0.50 g (1.62 mmol)) were dissolved in 10 ml of acetic acid at a temperature of 70° C., and the solution was left at room temperature for 3 days.

The precipitated crystals were separated by suction filtration, washed with a small quantity of acetic acid and dried in vacuo to obtain 0.30 g crystals. The obtained crystals was confirmed to be 96.9% pure N-formyl-α-L-aspartyl-L-phenylalanine by the HPLC analysis.

EXAMPLE 3

N-formyl-L-aspartic anhydride 1.50 g (10.5 mmol) was added to 15 ml of glacial acetic acid, and the solution was heated to 45° C. and stirred. To the solution was added 1.68 g (10.2 mmol) of D,L-phenylalanine over a period of 20 minutes, and the mixed solution was stirred continuously at the same temperature for one hour and then allowed to stand at room temperature for 3 days.

The precipitated crystals were separated by suction filtration, washed with a small quantity of acetic acid and dried in vacuo. The yield was 0.68 g. The result of HPLC analysis showed that the product was 94.6% pure N-formyl-α-L-aspartyl-L-phenylalanine.

EXAMPLE 4

N-formyl-L-aspartic anhydride (3.00 g (21.0 mmol)) was added to 15 ml of glacial acetic acid, and the solution was heated to 45° C. and stirred. To this solution was added 1.68 g (10.2 mmol) of D,L-phenylalanine over a period of 20 minutes, and the mixed solution was stirred continuously at the same temperature for one hour and then left at room temperature for 4 days.

The precipitated crystals were separated by suction filtration, washed with a small quantity of acetic acid and dried in vacuo. The yield was 0.77 g. The result of HPLC analysis showed that this product is N-formyl-α-L-aspartyl-L-phenylalanine of a purity of 95.3%.

EXAMPLE 5

N-formyl-L-aspartic anhydride (2.63 g (18.4 mmol)) was added to 13 ml of glacial acetic acid, and the mixture was stirred at 60° C. To this solution was added 2.94 g (17.8 mmol) of D,L-phenylalanine over a period of 20 minutes, and the mixed solution was stirred at the same temperature for one hour and then further stirred at room temperature overnight.

The precipitated crystals were separated by suction filtration, washed with a small quantity of acetic acid and dried in vacuo. The yield was 1.24 g. The product was confirmed to be 92.0% pure N-formyl-α-L-aspartyl-L-phenylalanine by HPLC analysis.

EXAMPLE 6

D,L-phenylalanine (1.73 g (10.4 mmol)) was added to 15 ml of glacial acetic acid, and the mixture was stirred at 35° C. To this solution was added 1.50 g (10.5 mmol) of N-formyl-L-aspartic anhydride over a period of 30 minutes, and the mixed solution was stirred at the same temperature for one hour and then left at room temperature for 5 days.

The precipitated crystals were separated by suction filtration, washed with a small quantity of acetic acid and dried in vacuo. The yield was 0.56 g. The result of HPLC analysis showed that the product was N-formyl-α-L-aspartyl-L-phenylalanine of a purity of 94.8%.

EXAMPLE 7

N-formyl-L-aspartic anhydride (1.50 g (10.5 mmol)) was added to a mixed solvent comprising 20 ml of glacial acetic acid and 5 ml of ethyl acetate, and the mixture was stirred at 45° C. To this solution was added 1.73 g (10.4 mmol) of D,L-phenylalanine over a period of 70 minutes, and the mixed solution was stirred at the same temperature for one hour and then left at room temperature for 4 days.

The precipitated crystals were separated by suction filtration, washed with a small quantity of acetic acid and dried in vacuo. The yield was 0.34 g. The result of HPLC analysis showed that the product was 91.3% pure N-formyl-α-L-aspartyl-L-phenylalanine.

EXAMPLE 8

Glacial acetic acid (10 ml) and acetic anhydride (1.6 ml) were added to 2.36 g (15.0 mmol) of N-acetyl-L-aspartic acid, and the mixture was stirred at room temperature for 5 hours. The resulting slurry reaction solution was heated to 40° C. and 2.47 g (15.0 mmol) of D,L-phenylalanine was added thereto over a period of 90 minutes. The mixed solution was cooled to room temperature, then added with 10 ml of diethyl ether and 5 ml of hexane and left at room temperature for 6 days.

The precipitated crystals were separated by suction filtration, washed with a small quantity of acetic acid and dried in vacuo. The yield was 0.72 g. The product was identified as 91.5% pure N-acetyl-α-L-aspartyl-L-phenylalanine by HPLC analysis.

EXAMPLE 9

D,L-phenylalanine (4.00 g (24.2 mmol)) was added to 30 ml of water, and the solution was adjusted to a pH of 12 with 5N NaOH and cooled to −10° C. To this solution was added 3.98 g (27.8 mmol) of N-formyl-L-aspartic anhydride over a period of 30 minutes. During this period, the pH of the solution was maintained at 11 to 13 and the temperature at −5° to −10° C. One hour later, the temperature of the solution was raised to room temperature and the pH thereof was reduced to 3.0 with 1N HCl. One hour thereafter, the pH of the solution was further reduced to 1.0 with 1N HCl.

The solution was left overnight and the precipitated crystals were separated by suction filtration, washed with a small quantity of water and dried in vacuo. The yield was 2.87 g. The result of HPLC analysis showed that the product was 97.1% pure N-formyl-α-L-aspartyl-L-phenylalanine.

What is claimed is:

1. A process for separating N-acyl-α-L-aspartyl-L-phenylalanine, which comprises selectively crystallizing N-acyl-α-L-aspartyl-L-phenylalanine from an acetic solution or an aqueous solution of N-acyl-α-L-aspartyl-L-phenylalanine containing (1)N-acyl-α-L-aspartyl-D-phenylalanine, (2)N-acyl-α-L-aspartyl-D-phenylalanine and N-acyl-β-L-aspartyl-L-phenylalanine, (3)N-acyl-α-L-aspartyl-D-phenylalanine and N-acyl-β-L-aspartyl-D-phenylalanine, or (4)N-acyl-α-L-aspartyl-D-phenylalanine, N-acyl-β-L-aspartyl-L-phenylalanine and N-acyl-β-L-aspartyl-D-phenylalanine at a temperature of −5° to 50° C.

2. The process according to claim 1, wherein the pH of said aqueous solution is 1.0 to 3.5.

3. The process according to claim 1, wherein said acetic solution is a reaction solution produced after condensing N-protected-L-aspartic anhydride and D,L-phenylalanine in an acetic solvent.

4. The process according to claim 3, wherein said condensation is carried out at a temperature of 0° to 60° C.

5. The process according to claim 1, wherein said aqueous solution is a reaction solution produced after condensing N-protected-L-aspartic anhydride and D,L-phenylalanine in an aqueous solvent while maintaining the pH at 7 or above and the temperature at 30° C. or below and then acidified.

6. The process according to claim 5, wherien the pH of said acidified reaction solution is 1.0 to 3.5.

* * * * *